United States Patent [19]

Norton

[11] 4,055,587
[45] Oct. 25, 1977

[54] AMMOXIDATION OF ALKYL SUBSTITUTED ORGANIC COMPOUNDS USING A SOLUTION OF AMMONIUM CARBONATE AS THE AMMONIA SOURCE

[75] Inventor: Richard V. Norton, Wilmington, Del.

[73] Assignee: Suntech, Inc., St. Davids, Pa.

[21] Appl. No.: 714,730

[22] Filed: Aug. 16, 1976

[51] Int. Cl.$^2$ ............................................. C07C 120/14
[52] U.S. Cl. ................................................. 260/465 C
[58] Field of Search ................................. 260/465 C

[56] References Cited

U.S. PATENT DOCUMENTS

| 3,462,476 | 8/1969 | O'Donnell et al. | 260/465 |
| 3,594,987 | 7/1971 | Oda et al. | 260/465 X |

Primary Examiner—Dolph H. Torrence

Attorney, Agent, or Firm—J. E. Hess; D. R. Johnson; P. Lipsitz

[57] ABSTRACT

In the process of converting alkyl substituted aromatic hydrocarbon to nitriles by ammoxidation where the aromatic hydrocarbon compound, oxygen and ammonia are reacted in the presence of an ammoxidation catalyst under ammoxidation conditions to obtain the nitrile, the improvement of supplying the total amount of ammonia reactant to the reactor as an aqueous solution of ammonia, carbon dioxide and their hydrolysis products (e.g. an ammonium carbonate solution). The major advantage of the process is that it achieves excellent conversion to nitrile without excessive burn of ammonia or organic reactant and avoids the necessity to separate ammonia from off-gases since the aqueous ammonia and carbonate containing solution is suitable for recycle.

9 Claims, No Drawings

AMMOXIDATION OF ALKYL SUBSTITUTED ORGANIC COMPOUNDS USING A SOLUTION OF AMMONIUM CARBONATE AS THE AMMONIA SOURCE

The vapor phase ammoxidation of organic compounds to nitriles is well known and is exemplitied by U.S. Pat. No. 2,463,457 (Denton, assigned to Socony-Vacuum Oil Co., issued Mar. 1, 1949) and by U.S. Pat. No. 2,496,661 (Denton, assigned to Socony-Vacuum Oil Co., issued Feb. 7, 1950). This process is useful for preparing nitriles of aromatic hydrocarbons, as for example, conversion of toluene to benzonitrile, xylenes to tolunitriles and phthalonitriles, and the like, and is also of value generally for converting alkyl substituted aliphatic, aromatic, alicyclic, and heterocyclic compounds to the corresponding nitriles. Basically, such process involves the feeding of reactant vapors (e.g., hydrocarbon, ammonia and air) to a reactor containing an ammoxidation catalyst where conversion of an alkyl group to a nitrile radical occurs. Generally, there is an excess of reactants and unreacted materials must be separated from products and recycled.

Numerous variations in the above described process have been developed and one of particular interest is that disclosed in U.S. Pat. No. 3,462,476 where the injection of water to the ammoxidation reactor is shown to be beneficial in increasing the yield of nitrile and in reducing hydrocarbon and ammonia burn. This patent discloses the recovery of recycle ammonia by steam stripping and its recycle together with small, by-product amounts of carbon dioxide and water to the ammoxidation reactor. In the operation of such processes on a commercial scale it is necessary to recover and recycle the excess ammonia and this requires large investment and operating expense for separators to remove ammonia vapors from the acidic gases and recirculate gaseous ammonia to the ammoxidation reactor. Such large expense is inherent in all gaseous ammonia separation systems because of the difficulty in removing ammonia from its aqueous solution with $CO_2$ and HCN.

The present invention provides a novel system which obviates the necessity for separating ammonia vapors and thus significantly reduces the costs of the overall ammoxidation process. In accord with the invention, ammoxidation of organic compounds is carried out in the presence of an ammoxidation catalyst and oxygen by supplying the total amount of ammonia reactant as an aqueous solution of ammonia, carbon dioxide and their hydrolysis products (e.g. an ammonium carbonate solution). The invention also embodies a continuous ammoxidation system as described where recycle ammonia in the form of its aqueous ammonium carbonate solution and its hydrolysis products is recycled to the reactor, thus eliminating the need for an expensive gaseous separation system for ammonia.

In carrying out the process of the invention, the reactor and attendant equipment is prepared in the usual way, the reactor being charged with catalyst and otherwise prepared for start-up. The reactants are passed over the catalyst at reaction conditions which will be about 300° to about 600° C and at pressures ranging from atmospheric to about 100 psig. Preferred treatment conditions will be about 400° to about 450° C at pressures of from atmospheric to about 50 psig.

It is understood that the ammoxidation reaction conditions need little change, if any, from those normally used as disclosed above and in the numerous well known patent and literature references, including the patents mentioned above. It will be necessary, however, to adjust the volumetric flow rate of the ammonia/$CO_2$ solution to get the desired contact time over the catalyst.

It will be understood that the process of the invention may be of the type where oxygen, usually in the form of air, is added to the system or alternatively, a "reactive-catalyst" may be used which supplies the oxygen in situ (See, for example, U.S. Pat. No. 3,479,385 issued Nov. 18, 1969 in the name of D. Th. A. Huibers and assigned to the Lummus Company). Likewise, the process is applicable to fixed bed and fluidized bed systems of operation. Preferred catalyst systems will be the numerous well-known ammoxidation catalysts such as the oxides of molybdenum, vanadium, tungsten, and the like. Also, other materials such as uranyl molybdate, iron, lead, sodium and copper molybdates and mixed catalysts may be used. A particularly preferred system where oxygen is employed in the feed stream is that using as catalysts the alkali-metal vanadium bronzes disclosed in U.S. Pat. No. 3,959,337, issued May 25, 1976 in the name of Bushick et al.

The mole ratio of reactants used in the process will likewise be in accord with the prior art teachings. Generally, the mole ratios of ammonia to hydrocarbon and of oxygen to hydrocarbon will be from about 2.5:1 to about 15:1 preferably no more than about 6.1 in the interests of economy. Most preferably molar ratios of about 3:1 to 5:1 will be used and these low ratios will be used in conjunction with the alkali-metal vanadium bronze catalysts referred to above. Generally, the procedure is to determine the ammonia to organic reactant ratio without water or $CO_2$ and the replace the pure $NH_3$ with a solution of $NH_3/CO_2$ to supply the quantity of $NH_3$ desired.

The concentration of the $NH_3/CO_2$ aqueous system is a variable that needs optimization for each catalyst. Preferably, the most concentrated system that gives the desired yield of nitirles is preferred. Excess water tends to generate amides from the nitriles so the most concentrated system consistent with the equipment is desired.

The ammonia is, of course, not necessarily in a stoichiometric quantity with $CO_2$. A series of solution equilibria describes the system rather than being ammonium carbonate or bicarbonate. The equilibria are as follows:

$$H_2O \rightleftarrows H_3O^+ + OH^-$$

$$NH_3 + H_2O \rightleftarrows NH_4OH$$

$$NH_4OH \rightleftarrows NH_4^+ + OH^-$$

$$CO_2 + H_2O \rightleftarrows H_2CO_3$$

$$H_2O + H_2CO_3 \rightleftarrows H_3O^+ + HCO_3^-$$

$$HCO_3^- + H_2O \rightleftarrows H_3O^+ + CO_3^-$$

$$CO_2 + NH_3 \rightleftarrows NH_2COOH$$

$$NH_2COOH + H_2O \rightleftarrows H_3O^+ + NH_2COO^-$$

The system is thus not simply $(NH_4)_2CO_3$ or $NH_4HCO_3$ but a very complex one that can serve as source of ammonia from the aqueous phase under ammoxidation conditions.

The partial pressure of ammonia over a solution of ammonia and $CO_2$ up to 4 mole % at 20° and 40° C was reported by Pexton and Badger. (J. Chem. Ind. 57, 106

(1938). Van Krevelen repeated some of these experiments and conducted new work at 60° C. (Van Krevelen, Hoftizzer and Huntzens (Rec. trav. chin de Pays Bags, 68, 191 (1949). TAKAHASHI (J. Chem. Soc. Japan 65, 837 (1962) studied the system at 28 Psi and 216 psi and considered the species present as ammonia, ammonium carbamate and water. His model neglected all other equilibria in the liquid phase

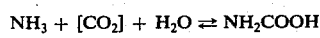

Van Krevelen, however, assumed that carbamic acid does not exist in solution and its ionization is infinite.

Thus, the species in aqueous solution are a complicated mixture dependent upon temperature, pressure, mole ratio of reactants, and concentration. Calling the system $NH_4HCO_3$ or $(NH_4)_2CO_3$ is not entirely accurate and for that reason the term $NH_3/CO_2$ is used herein.

It has been found that the molar ratio of carbon dioxide to ammonia must be within a specific range of from about 0.42:1 to about 1.33:1 in order to obtain the high yields. If the $CO_2$ to $NH_3$ ratio is either above or below this range yield of nitrile products drops significantly. Preferably, a mole ratio of about 0.5:1 will be used to get maximum yield. However, the process is operable above and below these parameters.

The aqueous solution is preferably maintained as such by addition of sufficient water or maintaining the system under pressure and heating for it to be homogeneous.

The aqueous solution of ammonium carbonate which is fed to the ammoxidation is accord with the process of the invention will be of a concentration to provide the required amount of ammonia for the reaction. Thus, in a preferred procedure the amount of ammonia and carbon dioxide present will be sufficient to provide from about three to about five moles of ammonia per mole of hydrocarbon reactant fed. The moles of $CO_2$ will generally be one-half the moles of ammonia and should not exceed the moles of $NH_3$. The carbonate solution is simple fed into the ammoxidation reactor as a spray and is, of course, vaporized in the reactor at the reactor temperature.

The effluent from the reactor will comprise the nitrile products, unreacted hydrocarbon, and vapors of water, $NH_3$, $CO_2$, $N_2$, and $O_2$. After separation of the products and excess hydrocarbon, the gaseous steam is comixed with water at 25°–80° C and the $N_2$ and $O_2$ taken overhead. The remaining liquid will be an aqueous ammonia/$CO_2$ solution and this, together with make up ammonia to bring the ammonia concentration up to required strength or concentration to adjust to the optimum $NH_3/CO_2$ ratio, will be recycled to the ammoxidation reactor.

The organic reactants most useful in the process will be alkyl substituted aromatic hydrocarbons, particularly those of the benzene and naphthalene series. Among preferred starting materials are the mono- and polyalkyl-substituted aromatic hydrocarbons such as toluene, the xylenes, α-methylnaphthalene, polymethylnaphthalenes, and the like. The alkyl substituent may, of course, contain more than a single carbon atom and thus the corresponding ethyl and other lower alkyl substituents are also useful. Most preferably the process will be used with p- and m-xylene, 2,4- and 2,6-dimethylnaphthalenes, and the like. The process is of significant value for the preparation of isophthalonitrile and terepgthalonitrile which are commercial products used as film and fiber intermediates.

In order to further illustrate the invention the following examples are given:

EXAMPLE 1—Control

Using a standard fixed-bed ammoxidation unit with a split core heating unit the following conditions are used for ammoxidation of p-xylene with a catalyst of 8% sodium-vanadium-bronze plus 0.7% $P_2O_5$ on an α-alumina support:

| | |
|---|---|
| Contact Time | 7.4 sec. |
| Moles $NH_3$/p-xylene | 3.8 |
| Moles $O_2$ (air)/p-xylene | 2.5 |
| Temperature = 419° C | |

The results which are obtained are given in the following table:

| | FEEDSTOCK | EFFLUENT |
|---|---|---|
| p-xylene | 1. mole | 0.461 moles |
| $NH_3$ | 3.8 moles | 2.05 moles |
| $O_2$ | 2.5 moles | 0.11 moles |
| $N_2$ | 10. moles | 10.52 moles |
| $CO_2$ + CO | | 0.43 moles |
| $H_2O$ | | 4.03 moles |
| Terephthalonitrile (TPN) | | 0.24 moles |
| Tolunitrile (TN) | | 0.24 moles |
| TOTAL | 17.30 moles | 18.07 moles |
| CONVERSION | | |
| of p-xylene | 53.9 mole % of Feed | |
| to Tolunitrile (TN) | 44.7 % | |
| to Terephthalonitrile (TPN) | 44.6 % | |
| $NH_3$ Burn | 27.1 % | |
| Temperature Rise | From 419° C to 465° C | |

It should be noted that the product split is equimolar TPN and TN, that the temperature exotherm rises approximately 40° C above the control setting, and that a considerable portion of the excess ammonia is burned (27.1%).

EXAMPLE 2

In the identical reactor as for Example 1, and using the same catalyst, a feed composition is used wherein all the ammonia is chemically combined in solution of (nominally) ammonium bicarbonate, but the total molar quantities remain essentially the same in spite of the deletion of $N_2$ and addition of $CO_2$ + $H_2O$ into the feed.

The results of this example are shown in the following table:

| | FEEDSTOCK | EFFLUENT |
|---|---|---|
| p-xylene | 1 mole | 0.35 moles |
| $NH_3$ | 3.8 moles | 2.06 moles |
| $O_2$ | 2.5 moles | 0.406 moles |
| $N_2$ | 0 moles | 0.366 moles |
| $CO_2$ | 3.8 moles | 4.06 moles |
| $H_2O$ | 6.2 moles | 10.48 moles |
| TPN | 0 moles | 0.390 moles |
| TN | 0 moles | 0.227 moles |
| CONVERSION | | |
| of p-xylene | 65 % | |
| to Tolunitrile | 34 % | |
| to Terephthalonitrile | 60 % | |
| $NH_3$ Burn | 19.5 % | |
| Temperature Rise | From 420° C to 440° C | |

It should be noted that conversion to the desired terephthalonitrile is increased; ammonia burn is lower, and the temperature exotherm is less than in Example 1.

After separation of the p-xylene, TPN and TN from the effluent stream, the aqueous solution of $NH_3$ and $CO_2$ (the $N_2$ and $O_2$ passing as off gases) comprises:

| | |
|---|---|
| $NH_3$ | 2.06 moles |
| $CO_2$ | 4.06 moles |
| $H_2O$ | 10.48 moles | and is treated with 1.54 moles of ammonia and then is swept with steam to prepare a solution containing:

| | |
|---|---|
| $NH_3$ | 3.8 moles |
| $CO_2$ | 3.8 moles |
| $H_2O$ | 6.2 moles |

This recycle stream of ammonium carbonate cogeners is used as a feed to the ammoxidation reactor and gives essentially the same improved results as report in the above table.

EXAMPLE 3

Using the same operating conditions as for Example 1 but at a residence time of 4 seconds, a parametric study on the effect of $NH_3/CO_2$ ratio yields the following data:

| Moles Per Mole of Xylene Fed | | | | |
|---|---|---|---|---|
| $NH_3$ | $CO_2$ | Ratio $CO_2:NH_3$ | $H_2O$* | Combined TN & TPN Yield |
| 3 | 0 | — | 25 | 60% |
| 3 | 1 | 0.33:1 | 25 | 55% |
| 3 | 1.5 | 0.5:1 | 25 | 80% |
| 3 | 3 | 1:1 | 25 | 75% |
| 3 | 5 | 1.66:1 | 25 | 50% |
| 3 | 10 | 3.33:1 | 25 | 40% |

*Hot aqueous solution pressure fed into reactor

As can be seen from the above data, the yield of nitriles falls off when the above recited mole ratio range of $CO_2$ to $NH_3$ is exceeded.

EXAMPLE 4

Ammoxidation of 2,6-dimethylnaphthalene with a vanadium bronze catalyst at 420°–425° C gives a 12% yield increase when $NH_3$, $CO_2$, and $H_2O$ is added instead of pure $NH_3$ and under the same conditions as using pure ammonia. The molar ratios used in this ammoxidation are $NH_3$:hydrocarbon=8:1, $O_2$:hydrocarbon=2:1, and $NH_3:CO_2=1:1$.

The invention claimed is:

1. In the process of converting an alkyl-substituted hydrocarbon of the benzene or naphthalene series to a nitrile by ammoxidation where the hydrocarbon reactant, oxygen and ammonia are reacted over an ammoxidation catalyst under ammoxidation conditions to obtain the nitrile, the improvement of supplying the total amount of ammonia reactant to the reactor as an aqueous solution of ammonia and carbon dioxide.

2. In the process of converting an alkyl-substituted hydrocarbon of the benzene and naphthalene series to an ammoxidation where the hydrocarbon, oxygen and ammonia are passed over an ammoxidation catalyst under ammoxidation conditions to obtain the nitrile, the improvement of supplying the total amount of ammonia reactant to the reactor as an aqueous solution of ammonia and carbon dioxide, separating nitrile product and unreacted hydrocarbon from the cooled reactor effluent, adding $NH_3$ to the aqueous ammonia and carbon dioxide solution to make up the $NH_3$ consumed, and recycling the aqueous ammonia and carbon dioxide solution to the ammoxidation reactor.

3. The process of claim 1 where the mole ratio of carbon dioxide to ammonia is from about 0.42:1 to about 1.33:1.

4. The process of claim 3 where the carbon dioxide to ammonia ratio is about 1:2.

5. The process of claim 2 where the carbon dioxide to ammonia ratio is from about 0.42:1 to about 1.33:1.

6. The process of claim 5 where the carbon dioxide to ammonia ratio is about 1:2.

7. The process of claim 1 where the alkyl-substituted hydrocarbon is p-xylene.

8. The process of claim 3 where the alkyl-substituted hydrocarbon is p-xylene.

9. The process of claim 6 where the alkyl-substituted hydrocarbon is p-xylene.

* * * * *